(12) United States Patent
Shimizu et al.

(10) Patent No.: US 11,135,075 B2
(45) Date of Patent: Oct. 5, 2021

(54) BIOABSORBABLE STENT

(71) Applicants: KAKE EDUCATIONAL INSTITUTION OKAYAMA UNIVERSITY OF SCIENCE, Okayama (JP); Japan Medical Device Technology Co., LTD., Kumamoto (JP)

(72) Inventors: Ichiro Shimizu, Okayama (JP); Akira Wada, Kumamoto (JP); Makoto Sasaki, Kumamoto (JP)

(73) Assignees: KAKE EDUCATIONAL INSTITUTION OKAYAMA UNIVERSITY OF SCIENCE, Okayama (JP); JAPAN MEDICAL DEVICE TECHNOLOGY CO., LTD., Kumamoto (JP)

(*) Notice: Subject to any disclaimer, the term of this patent is extended or adjusted under 35 U.S.C. 154(b) by 57 days.

(21) Appl. No.: 16/525,123

(22) Filed: Jul. 29, 2019

(65) Prior Publication Data

US 2019/0350732 A1    Nov. 21, 2019

Related U.S. Application Data

(63) Continuation of application No. PCT/JP2018/002669, filed on Jan. 29, 2018.

(30) Foreign Application Priority Data

Feb. 1, 2017   (JP) .............................. JP2017-017130

(51) Int. Cl.
    *A61F 2/915*    (2013.01)
(52) U.S. Cl.
    CPC .... *A61F 2/915* (2013.01); *A61F 2002/91583* (2013.01); *A61F 2210/0004* (2013.01); *A61F 2230/0013* (2013.01)

(58) Field of Classification Search
    CPC combination set(s) only.
    See application file for complete search history.

(56) References Cited

U.S. PATENT DOCUMENTS

| 5,776,161 A | * | 7/1998 | Globerman | ............... A61F 2/90 |
| | | | | 606/192 |
| 6,613,079 B1 | | 9/2003 | Wolinsky et al. | |

(Continued)

FOREIGN PATENT DOCUMENTS

| CN | 202568545 U | 12/2012 |
| CN | 104921854 A | 9/2015 |

(Continued)

OTHER PUBLICATIONS

Chinese Office Action, and English Translation thereof, for Chinese Application No. 201880009013.1, dated Apr. 16, 2020, (11 pages).

(Continued)

*Primary Examiner* — Jennifer Dieterle
*Assistant Examiner* — Danielle A. Stark
(74) *Attorney, Agent, or Firm* — Kagan Binder, PLLC (57) ABSTRACT

To provide a bioabsorbable stent including: a first tubular unit containing a plurality of cells coupled to each other, each of the cells formed from substantially linear parts and a substantially circular arc part and having a substantially U shape which opens to one end in the axial direction of the stent; and a second tubular unit having the same shape as that of the first tubular unit, the second tubular unit containing a plurality of cells each of which has a substantially U shape which opens to a direction opposite to the opening direction of the opposing first cell. The first tubular unit and the second tubular unit are alternately arranged in sequence to surround a central axis of the stent. Coupling members couple substantially linear parts in some of the opposing cells in the respective neighboring tubular units.

11 Claims, 6 Drawing Sheets

(56) References Cited

U.S. PATENT DOCUMENTS

| | | | |
|---|---|---|---|
| 7,179,285 B2 | 2/2007 | Ikeuchi et al. | |
| 8,323,329 B2* | 12/2012 | Gale | A61L 31/06 623/1.16 |
| 8,882,827 B2 | 11/2014 | Feng et al. | |
| 8,974,514 B2 | 3/2015 | Anukhin et al. | |
| 9,393,135 B2 | 7/2016 | Burgermeister et al. | |
| 10,524,942 B2 | 1/2020 | Poehlmann et al. | |
| 2001/0044649 A1 | 11/2001 | Vallana et al. | |
| 2005/0080479 A1* | 4/2005 | Feng | A61F 2/91 623/1.15 |
| 2005/0085899 A1* | 4/2005 | Thornton | A61F 2/91 623/1.16 |
| 2006/0247758 A1* | 11/2006 | Krivoruchko | A61L 31/022 623/1.15 |
| 2007/0135899 A1 | 6/2007 | Burgermeister et al. | |
| 2008/0132995 A1 | 6/2008 | Burgermeister et al. | |
| 2013/0178928 A1 | 7/2013 | Vyas et al. | |
| 2014/0081371 A1 | 3/2014 | Poehlmann et al. | |
| 2014/0081373 A1* | 3/2014 | Limon | A61F 2/91 623/1.11 |
| 2014/0277378 A1* | 9/2014 | Lane | A61F 2/89 623/1.16 |
| 2016/0067070 A1 | 3/2016 | Boismier | |
| 2018/0014953 A1* | 1/2018 | Yang | A61F 2/915 |
| 2020/0405515 A1* | 12/2020 | Labrecque | A61F 2/915 |

FOREIGN PATENT DOCUMENTS

| | | | | |
|---|---|---|---|---|
| EP | 1212986 | A | 6/2002 | |
| EP | 2710984 | A1 | 3/2014 | |
| ES | 2207407 | A1 | 5/2004 | |
| JP | 3654627 | B | 6/2005 | |
| JP | 2007325921 | A | 12/2007 | |
| JP | 3145720 | U | 10/2008 | |
| JP | 2010521234 | A | 6/2010 | |
| JP | 2013539661 | A | 10/2013 | |
| JP | 5684133 | B2 | 3/2015 | |
| JP | 2015154925 | A | 8/2015 | |
| JP | 2016214633 | A | 12/2016 | |
| WO | 2007134222 | A2 | 11/2007 | |
| WO | 2016037115 | A | 3/2016 | |
| WO | WO-2016110875 | A1 * | 7/2016 | A61F 2/915 |

OTHER PUBLICATIONS

"Active (Registered Trademark); Paciltaxel Drug ElutingStent", Cordynamic, retrieved from the Internet on Oct. 24, 2016, (23 pages).
English Abstract for ES2207407A1.
English Abstract for JP3145720U.
English Abstract for JP3654627B.
English Abstract for JP5684133B2.
English Abstract for JP2007-325921A.
English Abstract for JP2013-539661A.
English Abstract for JP2015-154925A.
English Abstract for JP2016-214633A.
International Preliminary Report on Patentability and English Translation thereof for International Application No. PCT/JP2018/002669, dated Aug. 15, 2019 (10 pages).
European Extended Search Report for European Application No. 18748044.7, dated Oct. 23, 2020, (5 pages).

\* cited by examiner

BIOABSORBABLE STENT

CROSS REFERENCE TO THE RELATED APPLICATION

This application is a continuation application, under 35 U.S.C. § 111(a), of international application No. PCT/JP2018/002669, filed Jan. 29, 2018, which claims priority to Japanese patent application No. 2017-017130, filed Feb. 1, 2017, the entire disclosure of which is herein incorporated by reference as a part of this application.

FIELD OF THE INVENTION

The present invention relates to a bioabsorbable stent that is used for treating stenosis in lumens, such as blood vessels, in a living body and is gradually degraded in the living body. In particular, the present invention relates to a bioabsorbable stent that has sufficient strength, excellent durability, as well as bending flexibility.

BACKGROUND OF THE INVENTION

Recently, stent treatment has rapidly become common. In the stent treatment, a stenosis part in an artery (or lumen) affected by progression of arteriosclerosis is mechanically expanded with a balloon catheter and a metal stent is implanted in the lumen so as to recover blood flow in the artery. The stent applicable for such treatment has to satisfy the following three requirements. First, a compressed stent is mounted around a balloon which is attached to the distal end of a balloon catheter and is passed through a patient's winding artery to be conveyed to a lesion part or a stenosis part while passing along a guide wire which has been inserted into the artery in advance. Accordingly, such a stent must be flexible in order to pass through a winding and narrow artery. Second, the stent in the expanded state must have sufficient strength for supporting an artery wall or keeping a stenosis part open as well as have durability against repeated bending loads due to heart beat. Third, the stent inserted into a lesion part or a stenosis part would be removed (desirably, bio-absorbed) after completion of a predetermined function (performance). It should be noted that stents give their nominal diameters and are designed such that they demonstrate maximum performance when expanded close to the nominal diameters.

A conventionally known structure of a stent is shown in FIG. 1 of Patent Document 1. The stent shown in FIG. 1 of Patent Document 1 (a non-bioabsorbable metal stent made of, e.g., a stainless steel, a Ti—Ni alloy, or a Cu—Al—Mn alloy) includes: a plurality of cells 6 coupled in a circumferential direction, the plurality of cells 6 being arranged so as to surround a central axis of the stent 1 to form a ring unit 4; and substantially S-shaped coupling parts 5 coupling the opposing cells 6 of the neighboring ring units 4 (all-linked type).

Another stent structure is known as described in FIG. 1 of Patent Document 2. This stent (a non-bioabsorbable metal stent made of, e.g., a stainless steel, a Ni—Ti alloy, or a Cu—Al—Mn alloy) includes: a first tubular unit 3 including a first cell group having a plurality of first cells 2 coupled in a circumferential direction; and a second tubular unit 3' including a second cell group having a plurality of second cells 2' coupled in the circumferential direction, the first and second tubular units being alternately arranged so as to surround a central axis C1 of the stent; wherein some of the opposing cells in the neighboring first and second ring units 3, 3' are coupled by a coupling part 4; and each of the first cells 2 and second cells 2' have a symmetrical shape with each other with respect to the coupling part as the center in the axial direction of the stent, and the cells with the coupling part 4 have a slightly longer length than those of the cells without coupling part (partially-linked type).

There has been known, as an improved-type stent over the stent disclosed in Patent Document 2, a stent having a structure shown in Patent Document 3 (a non-bioabsorbable metal stent made of, e.g., a cobalt-chromium alloy, or a stainless steel). This stent has good expandability as well as improved bending durability by modifying the cell structure of coupling parts in the cells to overcome problem in expandability of the coupled structure in the stent of Patent Document 2.

There has been also known a structure shown in FIG. 1 of Patent Document 4. This stainless stent (a non-bioabsorbable metal stent) includes: a first tubular unit containing a plurality of cells coupled to each other, each of the cells formed from substantially linear parts and a substantially circular arc part and having a substantially U shape which opens to one end in the axial direction of the stent; and a second tubular unit having the same shape as that of the first tubular unit, the second tubular unit containing a plurality of cells coupled to each other, each of which has a substantially U shape which opens to a direction opposite to the opening direction of the opposing first cell. In the stent, the first tubular unit and the second tubular unit are alternately arranged in sequence so as to surround a central axis of the stent. The substantially linear parts in some of a plurality sets of the opposing cells constituting the neighboring tubular units are coupled by coupling members. The stent having this shape is implemented as Apolo Stent (produced by Iberhospitex SA).

CONVENTIONAL ART DOCUMENT

Patent Document

[Patent Document 1] Japan Patent No. 3654627
[Patent Document 2] Japan Utility Model Registration No. 3145720
[Patent Document 3] Japan Patent No. 5684133
[Patent Document 4] Spain Patent Publication No. 2207407

SUMMARY OF THE INVENTION

Problems to be Solved by the Invention

Since the stent according to Patent Document 1 is of the all-linked type, it does not have sufficient bending durability. In contrast, from evaluation of physical properties, the stent according to Patent Document 2 was found that it had sufficient bending durability under bending load, but was hardly expandable due to higher standard distension pressure at the time of stent expansion than that of the stent disclosed in Patent Document 1. Therefore, the stent disclosed in Patent Document 2 has a problem in expansibility. The stent disclosed in Patent Document 3 has an improved expansibility over that of the stent disclosed in Patent Document 2. However, in a stent of the partially-linked type in which opposing cells are partly coupled, since linked parts are located in each top of circular arc parts of opposing cells, due to the stress concentrated in the circular arc parts, this partially-linked type would result in insufficient durability and poor resistance to breakage if a stent is formed of a bioabsorbable metal having a lower mechanical strength.

A non-bioabsorbable stent made of, e.g., a stainless steel described in Patent Document 4 is characterized in that a coupling part is formed in such a way as to avoid a connection located in each top of the circular arc parts of the cells where stress is concentrated. However, in the case where this structure is applied to a stent made of a bioabsorbable metal having a lower mechanical strength, the stent in an expanded state may cause a crack of a base material or of a surface cover material on a base material at coupled portions in a coupling member or at a top of a circular arc part in the substantially U-shaped cell, or may generate a small gap in an interface between a base material and a surface-cover material. Such phenomena may be accompanied by local corrosion due to local pH rise and would result in detrimental loss of physical properties (particularly, radial force) of the base material.

Accordingly, the inventors of the present application define a problem to be solved by the invention as providing a bioabsorbable stent that has a stent scaffold formed of a bioabsorbable material such as pure magnesium and a magnesium alloy having a lower mechanical strength than that of conventional non-bioabsorbable materials such as a stainless steel. The target stent has excellent expansibility at the time of stent expansion, sufficient strength for supporting an artery wall to keep a stenosis part open, high flexibility for making it possible to be easily conveyed through a narrow winding artery, as well as excellent durability against repeated bending loads in the artery due to heart beat.

Means for Solving the Problems

As the result of the intensive study of stent shapes to solve the above problems, the inventors of the present application found that a bioabsorbable stent structure can be obtained which achieves balanced mechanical performance for both flexibility and supporting force (radial force), even if the stent is made of a bioabsorbable metal having a low strength, such as a magnesium alloy, and thereby achieved the present invention.

That is, the present invention relates to a bioabsorbable stent including: a first tubular unit containing a plurality of cells coupled to each other, each of the cells formed from substantially linear parts and a substantially circular arc part and having a substantially U shape which opens to one end in the axial direction of the stent; and a second tubular unit having the same shape as that of the first tubular unit, the second tubular unit containing a plurality of cells each of which has a substantially U shape which opens to a direction opposite to the opening direction of the opposing first cell, wherein the first tubular unit and the second tubular unit are alternately arranged in sequence so that a plurality of the first tubular units and the second tubular units surround a central axis of the stent; and wherein coupling members couple substantially linear parts in some of the opposing cells in the respective neighboring tubular units; a ratio of a width ($w_T$) of the cell line at the top of the circular arc part of the substantially U-shaped cell to a width ($w_S$) of the cell line at the substantially linear part of the same cell is selected within a range defined by the following formula (1); a ratio of a height (h) between neighboring top and bottom of the cell to a width (w) between the top and the bottom of the cell is selected within a range defined by the following formula (2); and a maximum principal stress ($\sigma_{max}$) at the time of expansion is selected to fall within a range defined by the following formula (3); and all of the cells constituting the first and second tubular units contain a bioabsorbable metal.

$$1.1 < \text{width } (w_T) \text{ of the cell line at the top of the circular arc part/width } (w_S) \text{ of the cell line at the substantially linear part} < 1.5 \quad (1)$$

$$0.12 < \text{cell height } (h)/\text{cell width } (w) < 1.3 \text{ (in the case of a nominal diameter)} \quad (2)$$

$$\text{Maximum principal stress } (\sigma_{max}) \text{ at the time of stent expansion} < \text{tensile strength } (S) \text{ of a cell constituting material} \quad (3)$$

In the bioabsorbable stent, the cell preferably has a thickness (t) selected so as to satisfy a range defined by the following formula (4).

$$0.06 \text{ mm} < t < 0.12 \text{ mm} \quad (4)$$

In the bioabsorbable stent, the circular arc part of the cell preferably has a radius of curvature ($r_O$) selected so as to satisfy a range defined by the following formula (5).

$$0.15 \text{ mm} < r_O < 0.30 \text{ mm} \quad (5)$$

In the bioabsorbable stent, the substantially linear part of the cell preferably has an inclination angle ($q_S$) with respect to a longitudinal direction of the stent, which is selected so as to satisfy a range defined by the following formula (6).

$$30° < q_S < 90° \text{ (in the case of a nominal diameter)} \quad (6)$$

In the bioabsorbable stent, the bioabsorbable metal is preferably pure magnesium or a magnesium alloy.

In the bioabsorbable stent, each of the coupling members preferably includes a substantially linear coupling part for coupling the opposing cells and curved connecting parts formed on respective ends of the substantially linear coupling part, the curved connecting parts being provided for connecting an end of the substantially linear coupling part to the opposing substantially linear part of the cell.

Each of the curved connecting parts in the coupling member is preferably connected to an intermediate portion of the substantially linear part of the cell.

The curved connecting part preferably has a line width larger than that of the substantially linear coupling part in the coupling member.

In the bioabsorbable stent, the curved connecting part in the coupling member preferably has a minimum radius of curvature in a range from 40 to 100 am.

The present invention encompasses any combination of at least two features disclosed in the claims and/or the specification and/or the drawings. In particular, any combination of two or more of the appended claims should be equally construed as included within the scope of the present invention.

Effect of the Invention

According to the present invention, each of the tubular units made of a bioabsorbable material includes a plurality of cells each having substantially linear parts; coupling members are provided to couple some of a plurality of sets of opposing cells in a first cell group and a second cell group, respectively, at substantially linear parts in the cells; a ratio of a width ($w_T$) of the cell line at a top of a circular arc part to a width ($w_S$) of the cell line at a substantially linear part as well as a ratio of a cell height (h) to a cell width (w) are selected so as to satisfy the formulae (1) and (2), respectively; and further, a maximum principal stress ($\sigma_{max}$) at the time of stent expansion is selected so as to be smaller than tensile strength (S) of a cell-constituting material. As a result, stress and torsion applied to the cells are uniformly distributed, which makes it possible to dramatically increase durability against bending load, without compromising flexibility.

Further, where a coupling member is located at an intermediate location of the substantially linear part of the cell, and the line width of the curbed connecting part in the coupling member, the part which connects to the cell is larger than the line width of the substantially linear coupling part of the coupling member. Accordingly, it is possible to uniformly bend the entire stent at the time of expansion with distributing stress in the stent. Furthermore, the curved connecting parts in the coupling member coupled to the intermediate locations in the linear parts of the cells have a predetermined radius of curvature; as well as the tips of the substantially U-shaped cells have a predetermined radius of curvature; so that it makes possible to prevent occurrence of cracks at locations where stress is concentrated at the time of stent expansion, to achieve good adhesion between a stent scaffold and a surface-cover material at the time of stent expansion even when a polymer cover material layer is formed on the stent scaffold, as well as to prevent local corrosion of the stent material.

BRIEF DESCRIPTION OF THE DRAWINGS

The present invention will be more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views. In the figures.

DESCRIPTION OF THE EMBODIMENTS

Shape of Stent Scaffold

Figure 1:
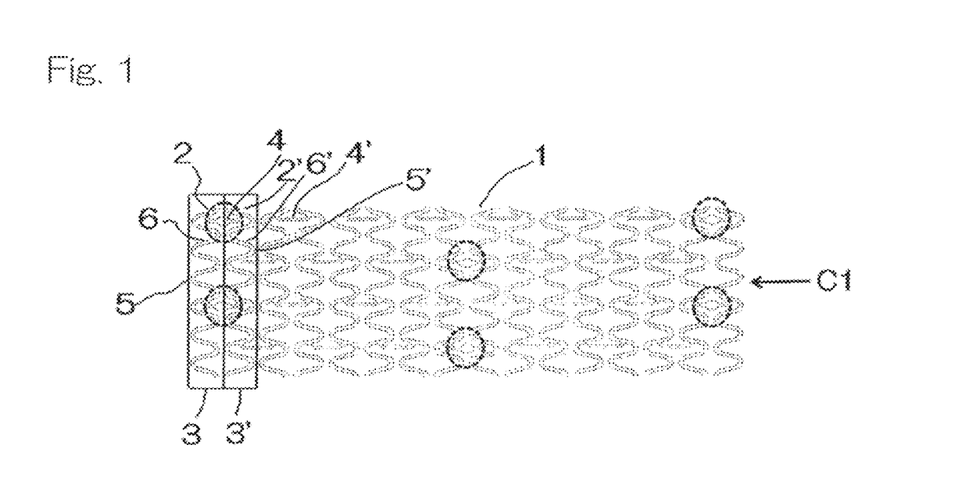
FIG. 1 is a plan view showing an example of a bioabsorbable stent according to the present invention.

In the embodiment shown in FIG. 1, a stent scaffold is formed into a substantially tubular shape. In the stent scaffold, a first tubular unit of a first cell group 3 (hereinafter sometimes referred to as first tubular unit 3) having a plurality of first cells 2 coupled in a circumferential direction and a second tubular unit of a second cell group 3' (hereinafter sometimes referred to as second tubular unit 3') having a plurality of second cells 2' coupled in the circumferential direction are connected (coupled) with coupling parts 4, 4' (or to connect some of the opposing cells in the neighboring tubular units 3, 3'). The coupling parts are preferably arranged at equivalent positions, for example, connected at 2 to 3 cells of the opposing cells in the neighboring tubular units. Each of the first cells 2 and second cells 2' have a symmetrical shape with each other with respect to the coupling parts 4, 4' as the center. A plurality of the tubular units 3, 3' are coupled by coupling parts so as to form a tubular body. The tubular units 3, 3' are stretchable in a radial direction from the inside of the tubular body. A plurality of the cells 2, 2' coupled in the circumferential direction are arranged in a plurality of rows to surround the central axis C1 of a stent 1 to form a stent scaffold having the tubular body.

In the shape of the stent scaffold shown in FIG. 1, each of the cells 2, 2' is a single constituting unit in a pattern constituting the stent 1. As shown in FIG. 1, cells are formed in a zig-zag shape in which each tip of the circular arc parts 5, 5' of the cells has a rounded shape having an acute angle. The stent shown in FIG. 1 is compressed such that all the cells 2, 2' are in parallel. The stent has a greater radial supporting force when the expanded stent has the cells 2, 2' with an obtuse angle at the circular arc parts in the direction of the central axis C1.

In the stent 1 which is exemplarily shown in FIG. 1, it is necessary to have at least one coupling part 4 or 4' between the cells 2, 2' constituting the tubular units (cell groups) 3, 3' in the circumferential direction of the stent 1. As the number of cells arranged in the circumferential direction depends on a stent diameter, the number of coupling parts may be selected in accordance with the number of cells. Typically, the number of the coupling parts is preferably from 2 to 3 in the case where the stent has a diameter from 3 to 9 mm and includes 6 to 10 cells in the circumferential direction. The rest of the cells 2, 2' are not coupled so as to form uncoupled parts. Provision of the uncoupled parts makes it possible to make the entire stent more flexible, to improve its deliverability to branched blood vessels, as well as to distribute the stress being applied to arch portions constituting coupling parts. Accordingly, the stent of this type has improved durability compared with a stent (of all-linked type) having coupling parts in a tightly arranged way.

Figure 2:
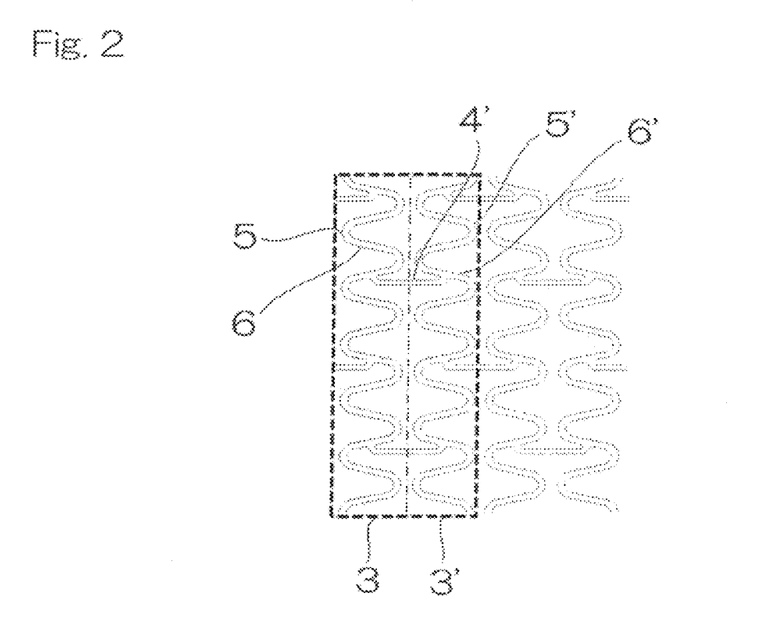
FIG. 2 is an enlarged view of coupling structures between cells in FIG. 1.

In the present invention, as shown in FIG. 2, coupling parts 4, 4' preferably couple the linear parts 6, 6' where stress is not concentrated, rather than coupling the circular arc parts 5, 5' of the cells 2, 2'.

Figure 3:
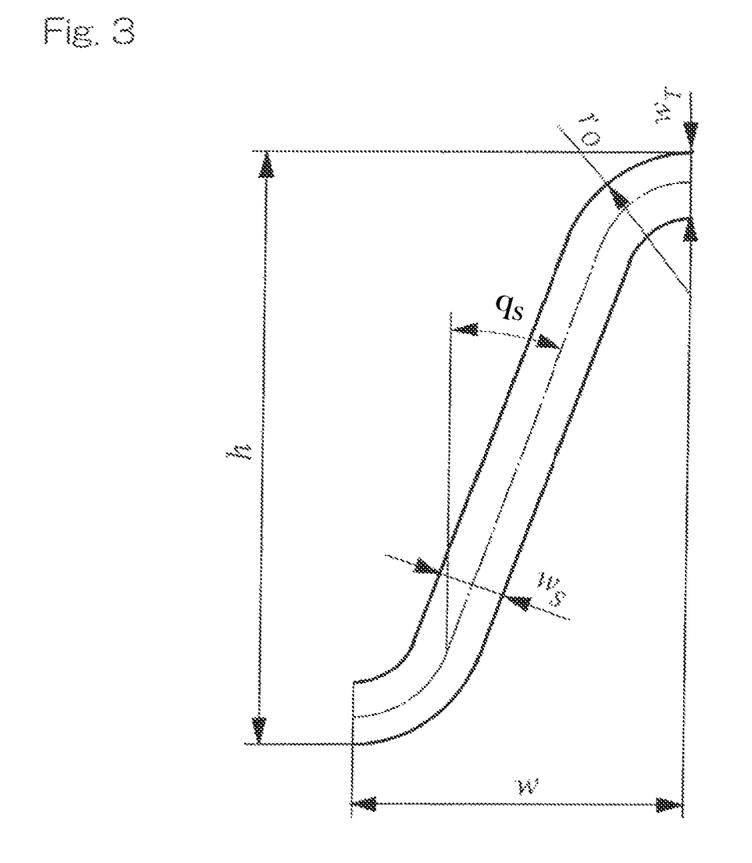
FIG. 3 is an enlarged view showing an example of a cell shape of a bioabsorbable stent according to the present invention.

FIG. 3 shows an enlarged view of a cell shape. FIG. 3 shows $w_T$ (width of the cell line at the top of the circular arc part), $w_S$ (width of the cell line at the substantially linear part), h (cell height), w (cell width), $r_O$ (radius of curvature of the circular arc part), $q_S$ (inclination angle of the linear part of the cell).

Formulae (1) to (3)

In the present invention, a ratio of a width ($w_T$) of the cell line at the top of the circular arc part of the substantially U-shaped cell to a width ($w_S$) of the cell line at the substantially linear part of the same cell is selected within a range defined by the following formula (1); a ratio of a height (h) between neighboring top and bottom of the cell to a width (w) between the top and the bottom of the cell is selected within a range defined by the following formula (2); and a maximum principal stress ($\sigma_{max}$) at the time of expansion falls within a range defined by the following formula (3).

1.1<width ($w_T$) of the cell line at the top of the circular arc part/width ($w_S$) of the cell line at the substantially linear part<1.5      (1)

Preferably, 1.1<width ($w_T$) of the cell line at the top of the circular arc part/width ($w_S$) of the cell line at the substantially linear part<1.3      (1')

0.12<cell height (h)/cell width (w)<1.3 (in the case of a nominal diameter)      (2)

Preferably, 0.35<cell height (h)/cell width (w)<1.2 (in the case of a nominal diameter)      (2')

Maximum principal stress ($\sigma_{max}$) at the time of stent expansion<tensile strength (S) of a cell constituting material      (3)

In the above formula (3), the tensile strength is shown as a value measured in accordance with ISO6892-1.

In the above formula (1), since the cell is subjected to higher stress at the top part of the circular arc part than at the linear part of the cell, as well as required to have flexibility at the linear part for expansion, it is necessary that the ratio of width ($w_T$) of the cell line at the top of the circular arc part/width ($w_S$) of the cell line at the substantially linear part falls within a range from 1.1 to 1.5.

In the case where the ratio is too small, the cell tends to be more likely to break because stress is concentrated on the circular arc top of the cell. In contrast, in the case where the ratio is too large, the substantially linear part of the cell tends to have insufficient flexibility because the width ($w_S$) is too large.

In the above formula (2), in the case where the ratio of cell height (h)/cell width (w) is too small, there is a tendency that the cell is subjected to increased maximum principal stress at the time of expansion so as to cause breakage in struts. In the case where the ratio is too large, a force in the radial direction tends to be insufficient, which would result in lower strength for supporting a blood vessel and may lead to restenosis.

Figure 4:
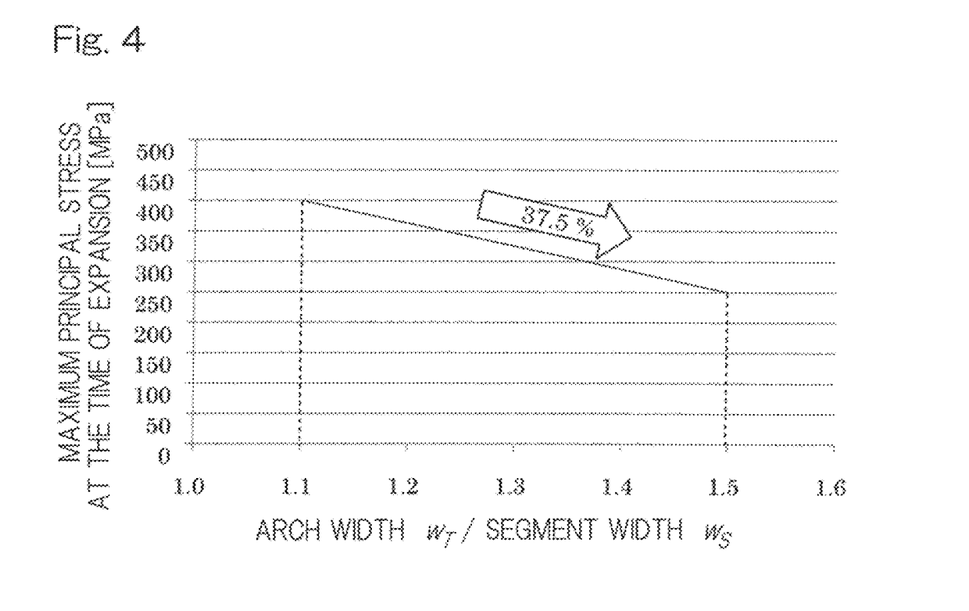
FIG. 4 is a graph showing an example of a relationship between a ratio of arch width/segment width (horizontal axis) and a maximum principal stress at the time of expansion (vertical axis) as for a cell in a bioabsorbable stent according to the present invention.
Figure 5:
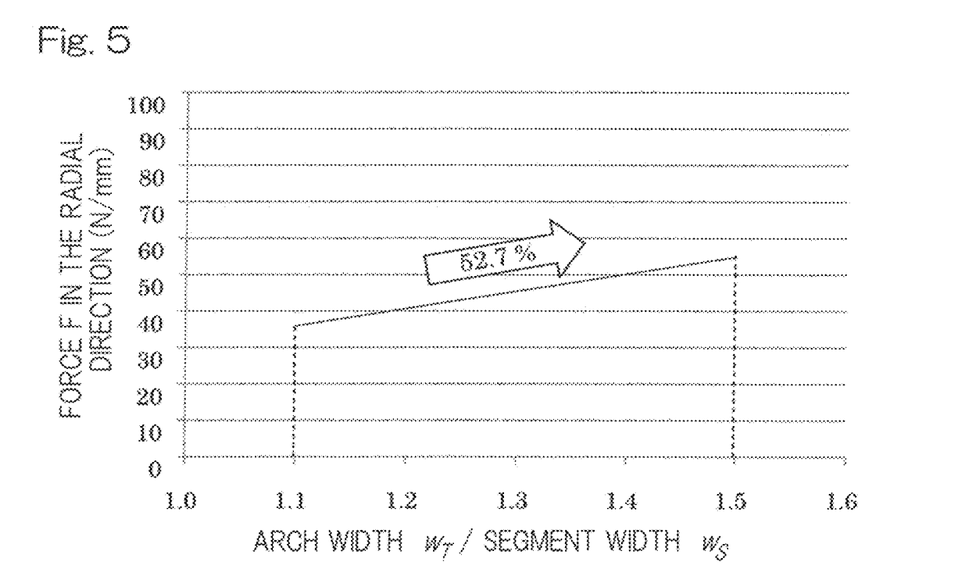
FIG. 5 is a graph showing an example of a relationship between a ratio of arch width/segment width (horizontal axis) and a force in the radial direction (vertical axis) as for a cell in a bioabsorbable stent according to the present invention.
Figure 6:
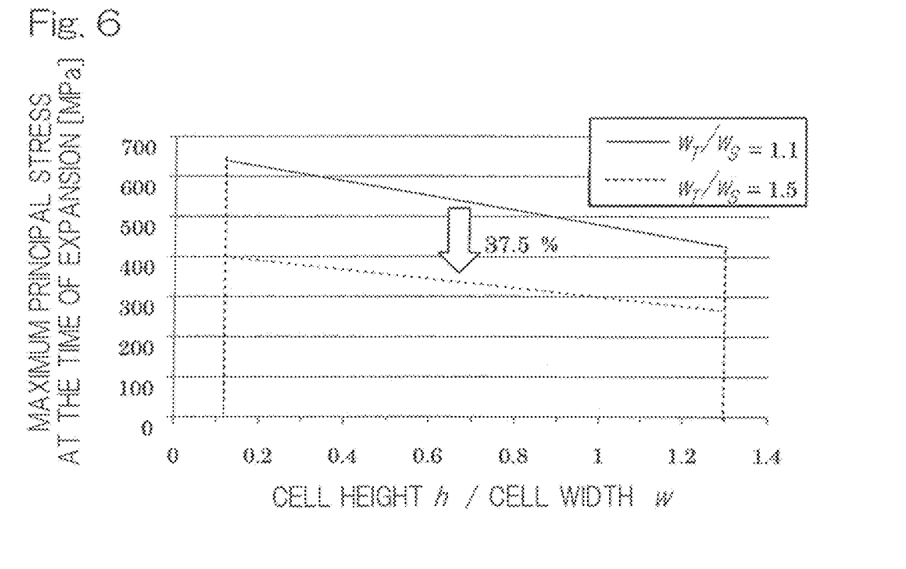
FIG. 6 is a graph showing an example of a relationship between a ratio of cell height/cell width (horizontal axis) and a maximum principal stress at the time of expansion (vertical axis) as for a cell in a bioabsorbable stent according to the present invention.

As for an example of the cells constituting a stent of the present invention, FIG. 4 shows change in maximum stress values (MPa) at the time of expansion of the stent depending on ratios of width ($w_T$) of the arch line (top of the circular arc part of the cell)/width ($w_S$) of the segment line (substantially linear part of the cell) from 1.1 to 1.5; and FIG. 5 shows change in force values (N/mm) in the radial direction depending on ratios of width ($w_T$) of the arch line (top of the circular arc part of the cell)/width ($w_S$) of the segment line (substantially linear part of the cell) from 1.1 to 1.5. FIG. 6 shows change in maximum stress (MPa) at the time of expansion depending on ratios of cell height (h)/cell width (w) from 0.12 to 1.3 for the respective cases where a ratio of a width ($w_T$) of the arch line (top of the circular arc part of the cell)/a width ($w_S$) of the segment line (substantially linear part of the cell) was set to (A) 1.1 as well as (B) 1.5, and FIG. 7 shows change in force in the radial direction depending on ratios of cell height (h)/cell width (w) from 0.12 to 1.3 for the respective cases where a ratio of a width ($w_T$) of the arch line (top of the circular arc part of the cell)/a width ($w_S$) of the segment line (substantially linear part of the cell) is set to (A) 1.1 as well as (B) 1.5.

The maximum principal stress at the time of expansion and force in the radial direction were evaluated using finite element analysis. In the analysis, a target model of a cell was subjected to deformations corresponding to (i) crimping to a balloon catheter, (ii) expansion, and then (iii) load (stress) removal so as to calculate the maximum principal stress (MPa) at the time of expansion. Further, deformation corresponding to load from a blood vessel was given to the model after the load removal to determine a force (N/mm) in the radial direction. The target model used herein was applied with a stress-strain relation of the magnesium alloy that was actually used in the experiments.

FIG. 4 shows that when the ratio of the arch width/the segment width was increased from 1.1 to 1.5, the value of the maximum principal stress at the time of expansion decreased by 37.5%, whereas FIG. 5 shows, in contrast, that the force in the radial direction increased by 52.7% and thus was in an inverse correlation. Where the increased value of the maximum principal stress at the time of expansion exceeds tensile strength of the material, such a stent cannot be practically used even though the ratio of the arch width/the segment width falls within the above range.

Figure 7:
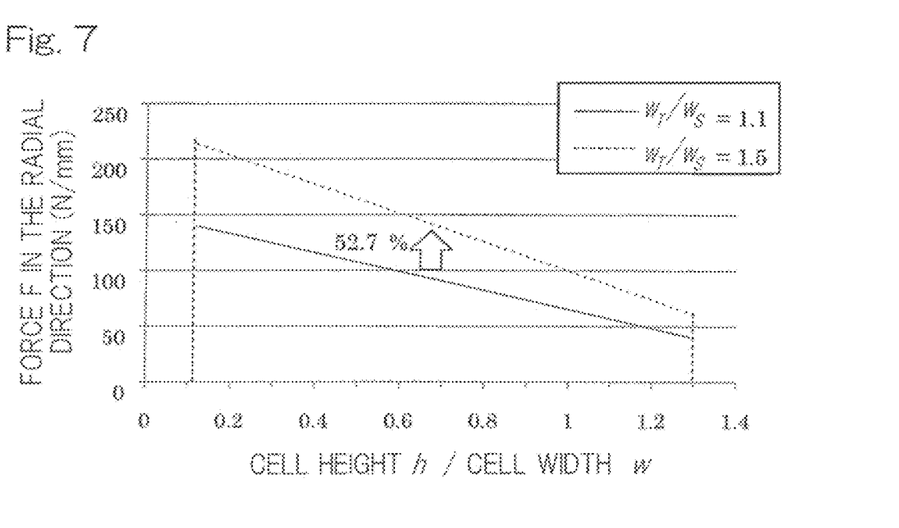
FIG. 7 is a graph showing an example of a relationship between a ratio of cell height/cell width (horizontal axis) and a force in the radial direction (vertical axis) as for a cell in a bioabsorbable stent according to the present invention.

FIGS. 6 to 7 show changes in the maximum principal stress at the time of expansion and in the force in the radial direction for the respective cases where the ratios of the arch width/the segment width were 1.1 and 1.5 when the ratio of the cell height/the cell width was increased from 0.12 to 1.3. In FIG. 6, where the ratio of the arch width/the segment width was 1.1, the maximum principal stress at the time of expansion exceeded the tensile strength of the magnesium alloy used (AZ31), i.e., 400 MPa, so that such a stent cannot be used even though the ratio of the arch width/the segment width falls within the range from 1.1 to 1.5. On the other hand, where the ratio of the arch width/the segment width was set to 1.5, the tensile strength (S) of the cell constituting material was able to be suppressed to 400 MPa or lower, as shown in FIG. 6. That is, the above formula (3) can be satisfied. From those results, the width ($w_T$) of the arch line (top of the circular arc part of the cell), the width ($w_S$) of the segment line (substantially linear part of the cell), the cell height (h) and the cell width (w) can be selected so as to satisfy the respective formulae (1) to (3) in order to obtain a stent having sufficient strength, excellent durability, flexibility as well as excellent expandability from a bioabsorbable metal.

To compare a stent of the present invention and a stent according to Patent Document 4, a photograph of Apolo Stent (Apolo 3) (made of stainless steel) in the document "Active (registered trademark); Paclitaxel Drug Eluting Stent" Cordynamic, retrieved from the Internet on Oct. 24, 2016 was used to calculate a value of a width ($w_T$) of the cell line at the top of a circular arc part/a width ($w_S$) of the cell line at the linear part required in the formula (1), and the calculated value was 0.9. The value of the cell height (h)/the cell width (w) in accordance with the formula (2) was calculated as 1.8.

This indicates difference in values of the main parameters for determining the stent shape between the Apolo Stent having a scaffold made of stainless steel and the bioabsorbable stent according to the present invention which is made of a bioabsorbable metal (a magnesium alloy) having significantly lower mechanical properties than those of stainless steel (Young's modulus is one fifth to one fourth of that of stainless steel). It should be noted that if a magnesium alloy is used for the scaffold of the Apolo Stent, such a stent would have significantly lower radial force when compared with that of the stent of the present invention, and thus cannot perform a predetermined function (performance) in a living body (see Example and Comparative Example described later).

In the bioabsorbable stent of the present invention, the cell preferably has a thickness (t) to satisfy the range defined by the following formula (4).

$$0.06 \text{ mm} < t < 0.12 \text{ mm} \quad (4)$$

More preferably, $$0.08 \text{ mm} < t < 0.11 \text{ mm} \quad (4')$$

In the case where the thickness (t) of the cell is too large, since the external surface of the stent scaffold would contact to a blood vessel wall, while the internal surface of the stent would be apart from the blood vessel wall by the height corresponding to the thickness, turbulent blood flow would be more likely to occur at each of the side surfaces of the stent scaffold, which may lead to restenosis and thrombosis due to generation of turbulent blood flow. Accordingly, an excessively large thickness is not preferable. In contrast, in the case where the thickness (t) of the cell is too small, this may result in insufficient supporting force in the radial direction and thus is not preferable.

In the bioabsorbable stent of the present invention, the cell preferably has a radius of curvature ($r_O$) at the circular arc part to satisfy the range defined by the following formula (5).

$$0.15 \text{ mm} < r_O < 0.30 \text{ mm} \quad (5)$$

More preferably, $$0.20 \text{ mm} < r_O < 0.28 \text{ mm} \quad (5')$$

In the case where the radius of curvature of the circular arc part is too small, there is a tendency that processability of such a stent through e.g. laser processing or electropolishing would cause difficulty. To the contrary, in the case where the radius of curvature is too large, an outer diameter when crimped would increase, resulting in decreased delivery performance of such a stent to an affected part. Accordingly, an extremely small or large radius of curvature is not preferable.

In the bioabsorbable stent of the present invention, the cell preferably has an inclination angle ($q_S$) of the linear part selected so as to satisfy the range defined by the following formula (6).

$$30° < q_S < 90° \text{ (in the case of a nominal diameter)} \quad (6)$$

More preferably, $$40° < q_S < 70° \text{ (in the case of a nominal diameter)} \quad (6')$$

In the case where the inclination angle is too small, the force in the radial direction tends to be insufficient, whereas in the case where it is too large, the maximum principal stress at the time of expansion tends to increase so that breakage of struts may be more likely to occur.

Figure 8:
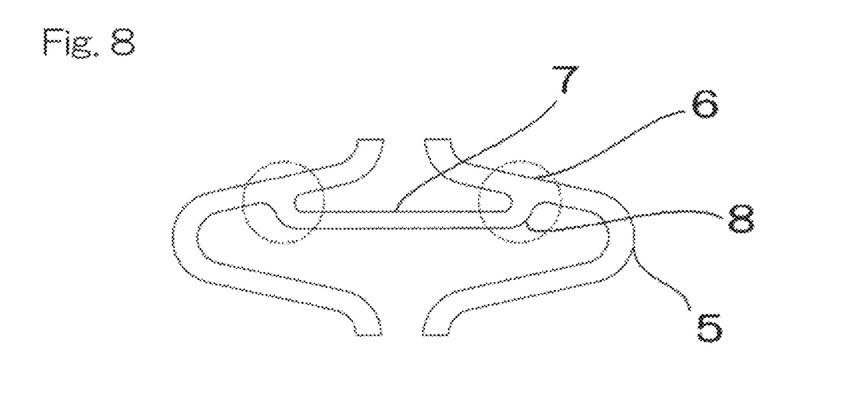
FIG. 8 is a plan view showing an example of coupling member of a bioabsorbable stent according to the present invention.
Figure 9:
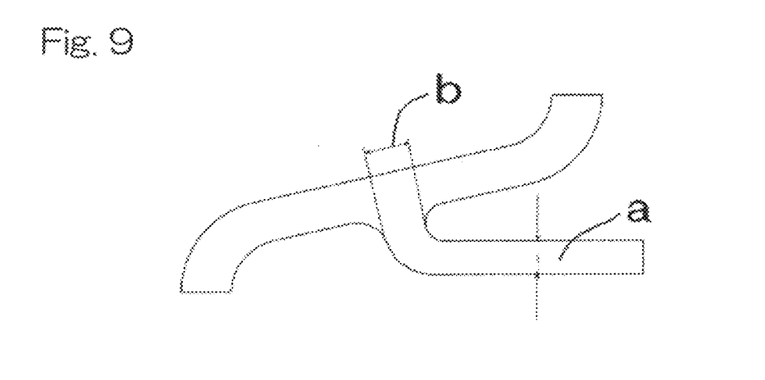
FIG. 9 is a plan view showing an example of a curved connecting part in the coupling member of a bioabsorbable stent according to the present invention.
Figure 10:
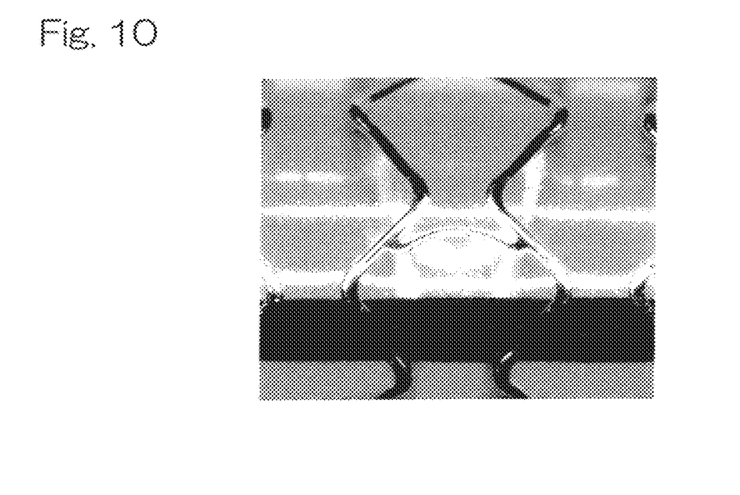
FIG. 10 is a photograph showing an external appearance of a linked shape after expansion of a bioabsorbable stent according to the present invention.

In the bioabsorbable stent of the present invention, the coupling member preferably has a substantially linear coupling part (7) for coupling the opposing cells; and curved connecting parts (8) formed on respective ends of the substantially linear coupling part (7). Each of the curved connecting parts connects an end of the substantially linear coupling part to the opposing substantially linear part of the cell (FIG. 8). Each of the curved connecting parts (8) in the coupling member is preferably connected to a substantially intermediate portion of the substantially linear part of the cell, the portion at which stress is not concentrated. Further, the curved connecting part preferably has a line width (b) that is larger than a line width (a) of the substantially linear coupling part (7) of the coupling member (FIG. 9). Thanks to the larger line width of the curved connecting part, the coupling member can be more rigidly fixed to the cell, and the substantially linear coupling part of the coupling member can be more easily deformed at the time of stent expansion (FIG. 10).

In the bioabsorbable stent of the present invention, the curved connecting part in the coupling member preferably has a minimum radius of curvature in a range from 40 to 100 jam, preferably from 50 to 90 am. In the case where the radius of curvature is too small, there is a tendency that processability through e.g. laser processing or electropolishing of such a stent causes difficulty. To the contrary, in the case where the radius of curvature is too large, an outer diameter at the time of crimping would increase, resulting in decreased delivery performance to an affected part.

Marker

In the bioabsorbable stent of the present invention, it is preferable to separately provide a marker in the stent scaffold because pure magnesium or magnesium alloys constituting the scaffold of the bioabsorbable stent have low X-ray contrast, which makes it difficult to confirm the location of the stent in blood vessels using an X-ray inspection apparatus. The marker is preferably provided at a central portion of the linear coupling part in the coupling member, the portion (location) where less stress is applied (see FIG. 1, the locations encircled with dashed lines; coupling part 4). As shown in FIG. 1, the central location of the linear part of the coupling member to which a marker is provided is widened so that the marker can be provided.

Bioabsorbable Metal

The stent of the present invention is formed from a metal that can be degraded in a living body (biodegradable metal). In the present invention, bioabsorbable metals constituting a stent scaffold may include metals that are degraded/absorbed in a living body such as, for example, pure magnesium and magnesium alloys.

Magnesium alloys contain magnesium as a main component (for example, 90 mass % or more, preferably 93 mass % or more, more preferably 95 mass % or more) and at least one element selected from the biocompatible element group consisting of Zr, Y, Ti, Ta, Nd, Nb, Zn, Ca, Al, Li, Ca, and Mn; or preferably at least one element selected from the biocompatible element group consisting of Zn, Zr, Mn, and Ca.

Cover Layer Additionally, the stent scaffold may be covered with a biodegradable polymer. Examples of the biodegradable polymers may include a poly-L-lactic acid (PLLA), a poly☐D,L-lactic acid (PDLLA), a poly(lactic acid-glycolic acid) (PLGA), a polyglycolic acid (PGA), a polycaprolactone (PCL), a polylactic acid-ε-caprolactone (PLCL), a poly(glycolic acid-ε-caprolactone) (PGCL), a poly-p-dioxanone, a poly(glycolic acid-trimethylene carbonate), a poly-β-hydroxybutyric acid, and others. In general, where these polymers have similar molecular weights, PCL and PLCL are preferable because these polymers have excellent flexibility and extensibility at 37° C. as well as excellent hydrophobicity, compared with other polymers.

The biodegradable polymer layer may contain a medicine such as, for example, an intimal thickening inhibitor (sirolimus, everolimus, biolimus A9, zotarolimus, paclitaxel, etc.).

The biodegradable polymer is dissolved in a suitable solvent and is spray-coated onto a stent scaffold to form a polymer cover layer on a surface of the stent scaffold.

Production of Stent

The stent of the present invention has a specific shape as described above, and a stent having such a shape can be integrally produced through laser processing. In the production process through laser processing, a tool path during laser processing is first created using a CAM on the basis of the data for a designed stent shape. The tool path can be set considering, for example, that the stent has shape retention after laser cutting as well as the procedure suppresses residual chips. Next, laser processing is performed to a thin-walled metal tube.

Since the present invention uses a bioabsorbable (biodegradable) metal as a stent material, it is preferable to use a method disclosed in JP Laid-open Patent Publication No. 2013-215487, in order to prevent thermal influence to the bioabsorbable metal. In the method, for example, a metal core rod is inserted into a hollow portion of a tubular stent material to form a rod-embraced tube so that the stent material can retain its linear shape. The rod-embraced tube is subjected to laser (water laser) processing in which the stent material is laser-processed in the presence of water sprout formed up to the stent material as a waveguide of the laser light so as to suppress thermal influence. Then, the metal core rod is removed from the processed tube.

After the stent material is formed into a mesh shape through laser cutting, the surface of the mesh shape is electropolished so as to have a mirror surface as well as to finish the edge portions into a smooth shape. In the stent production process, a post-processing step may be carried out after laser cutting. For example, oxides generated on the metal cut surface of the laser-cut stent may be dissolved with an acidic solution, and then the resultant is subjected to electropolishing. Since the present invention uses a bioabsorbable metal, in the electropolishing process, the stent and a metal plate such as stainless steel are immersed in an electrolyte, and the two metals are connected via a direct current power source. A voltage is applied to the stent on a cathode side and the metal plate on an anode side to dissolve the stent on the cathode side, achieving polishing effect. To obtain sufficient polishing effect, composition of the electrolyte and conditions of the current to be applied have to be considered for the process.

Since the laser processing method can form a stent with a desired mesh structure, it is possible to provide a stent that can sufficiently secure high flexibility and radial supporting force, enhance expandability of blood vessels, restrain a foreshortening and flare phenomenon, as well as avoid breakage of cells and others during use. Additionally, the stent suppresses generation of stress-concentrating area so that the stent scaffold and/or the polymer cover layer formed on the stent scaffold prevent cracks during expansion.

Hereinafter, the present invention will be specifically described by referring to Examples. It should be noted that the present invention be not limited to the following Examples.

EXAMPLE

Figure 11:
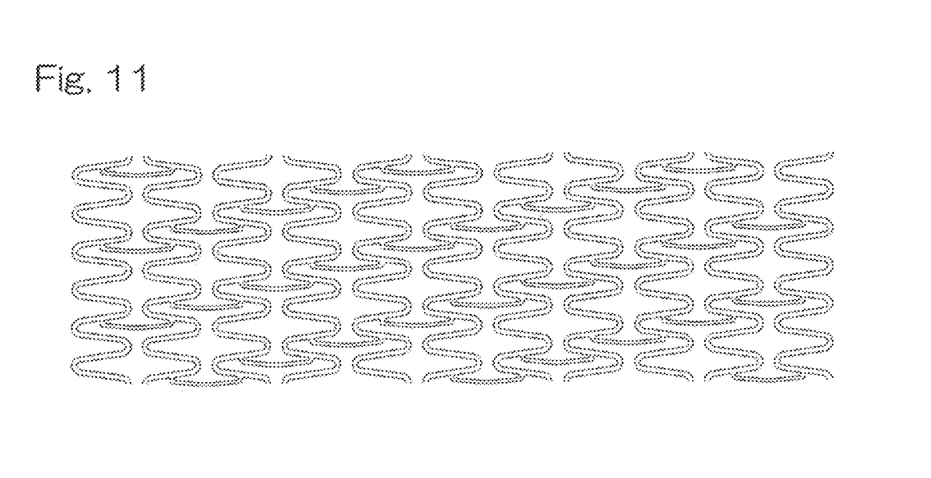
FIG. 11 is a plan view of a bioabsorbable stent used as a Comparative Example sample.

In Examples and Comparative Examples, bioabsorbable stents prepared in accordance with the manufacturing method described above were used. A thin-walled tube made of a magnesium alloy (AZ31) having a thickness of 150 μm (outer diameter of 1.8 mm/inner diameter of 1.5 mm) was processed through laser cutting to form a mesh shape; then, was processed through electropolishing to give a mirror surface and make the edged portions into a smooth shape. Thus obtained stent having a thickness of 100 μm (outer diameter of 1.75 mm/inner diameter of 1.55 mm) was placed (crimped) around a balloon attached at a distal end portion of a balloon catheter such that the stent has an outer diameter of 1.2 mm. The design shown in FIG. 1 was used for samples of Examples, and the design (having different dimensions at respective portions such as cell height, cell width from those of the stent according to the present invention) shown in FIG. 11 was used for samples of Comparative Examples.

Table 1 below shows respective sizes of the samples in Example and Comparative Example, including the width ($w_T$) of the cell line at the top of the circular arc part, width ($w_S$) of the cell line at the substantially linear part, cell height (h) and cell width (w) in the case where the stent has a nominal diameter, maximum principal stress ($\sigma_{max}$) at the time of stent expansion, tensile strength (S) of a cell constituting material, thickness (t) of the cell, radius of curvature ($r_O$) of the circular arc part of the cell, and inclination angle ($q_S$) of the substantially linear part of the cell.

TABLE 1

Dimensional values of Samples in Example and Comparative Example

| | Example | Comparative Example |
|---|---|---|
| $w_T$ (mm) | 0.1320 | 0.1125 |
| $w_S$ (mm) | 0.1100 | 0.1250 |
| h (mm) | 0.75 | 1.30 |
| w (mm) | 0.78 | 0.78 |
| $\sigma_{max}$ (MPa) | 321 | 313 |
| S (MPa) | 331 | 331 |
| t (mm) | 0.100 | 0.115 |
| $r_O$ (mm) | 0.25 | 0.15 |
| $q_S$ (°) | 46 | 30 |

Method for Evaluating Radial Force

Figure 12:
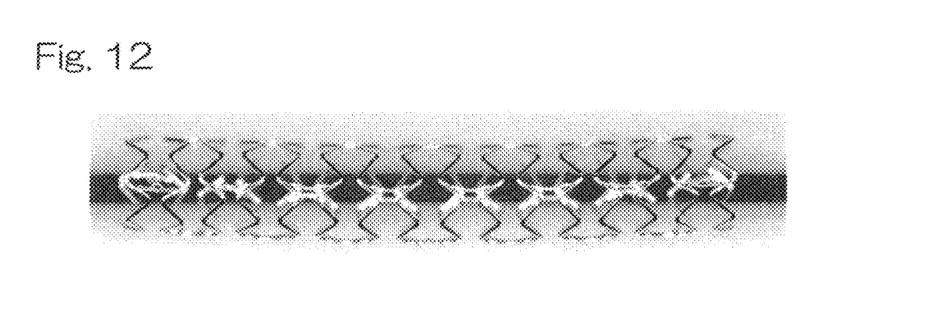
FIG. 12 is a photograph showing an external appearance of an example of a bioabsorbable stent according to the present invention, which is expanded to have an internal diameter of 3 mm.
Figure 13:
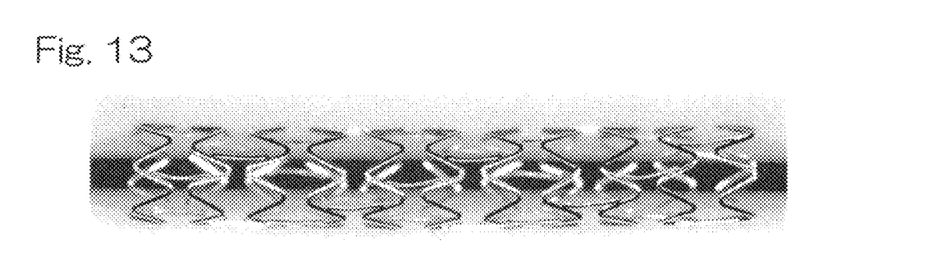
FIG. 13 is a photograph showing an external appearance of a bioabsorbable stent as a Comparative Example sample, which is expanded to have an internal diameter of 3 mm.

Each stent crimped on the balloon catheter was immersed in a PBS solution at 25° C. for 2 minutes and then was uniformly expanded to have an inner diameter of 3 mm. The stent was removed from the PBS solution, sufficiently ultrasonically cleaned with acetone, and dried at 60° C. for 24 hours under reduced pressure. The samples in Example (FIG. 12) and Comparative Example (FIG. 13) were confirmed that there was no damage (a crack or break) at the time of expansion using a microscope and were measured for radial force (n=3). A radial force testing machine [RX550/650 (produced by Machine Solutions)] was used for the measurement of radial force.

Pig Implantation Test

Each stent crimped on a balloon catheter was inserted in coronary arteries (LAD, LCX, RCA) of pigs (white pigs: 50 to 55 kg) and expanded at a site having a vascular lumen diameter of about 3 mm. Two out of three coronary arteries for each pig were selected, and two stents were implanted per pig.

TABLE 2

Combinations of Implantation Sites and Samples

|  | LAD | LCX | RCA |
| --- | --- | --- | --- |
| Pig 1 | Ex. Sample 1 | Com. Ex. Sample 1 | — |
| Pig 2 | — | Ex. Sample 2 | Com. Ex. Sample 2 |
| Pig 3 | Com. Ex. Sample 3 | — | Ex. Sample 3 |

Method for Evaluating Recoil Value in Pig Implantation Test

Immediately after implantation, it was confirmed that each stent closely touched a blood vessel wall, and then an inner area (lumen area) of the stent (a) was measured using an optical interference tomographic meter (OCT apparatus). At 7 days after implantation to the pigs, in each sample, the inner area of the stent (b) was measured in the same way. The stent was measured at points with intervals of 3 mm in a longitudinal direction, and an average value thereof was regarded as inner area of the stent. A reduction rate (recoil value) relative to an inner area of the stent immediately after implantation was calculated by the following formula (n=3).

Recoil Value=$(a-b)/a$

The evaluation results of the stents in the above Example and Comparative Example are shown below.

It was found that both of the stents with the design according to the present invention (Example samples) and the stents without the design according to the present invention (Comparative Example samples) (substantially corresponding to the design of Apolo Stent) were not injured (i.e., without crack or break) during crimping and expansion.

Results from Radial Force Measurement

The Example samples and Comparative Example samples had radial forces of 63.12±5.36 N/mm and 23.45±0.80 N/mm, respectively. The Example samples were found that they had equivalent radial force (40 to 70 N/mm) to those of commercially available (non-bioabsorbable) stents made of a cobalt-chromium alloy, even though they were made of a magnesium alloy. In contrast, the Comparative Example samples had lower radial force than 40% of that of the Example samples, and it was suggested that the Comparative Example samples did not satisfy the required level for stent radial force.

Results from Recoil Value Measurement

TABLE 3

Recoil Value at 7 Days After Stent Implantation

|  |  | Inner area of stent (mm$^2$) | | |
| --- | --- | --- | --- | --- |
|  |  | Immediately after implantation | 7 days after implantation | Recoil value (%) |
| Ex. Sample | 1 | 7.22 ± 0.19 | 6.98 ± 0.38 | 2.97 ± 0.35 |
|  | 2 | 7.22 ± 0.31 | 7.04 ± 0.35 |  |
|  | 3 | 7.09 ± 0.27 | 6.87 ± 0.45 |  |
| Com. Ex. Sample | 1 | 7.28 ± 0.31 | 5.21 ± 0.87 | 18.86 ± 6.92 |
|  | 2 | 7.17 ± 0.41 | 6.29 ± 0.55 |  |
|  | 3 | 7.11 ± 0.16 | 5.98 ± 0.62 |  |

Immediately after implantation to the pig coronary arteries, it was confirmed that both of the Example samples and Comparative Example samples closely touched blood vessel walls. There was no significant difference in inner areas among those stents. However, at 7 days after implantation, the Example samples did not show a substantial change, whereas the Comparative Example samples showed a significant decrease in inner area of the stent samples. As a result, regarding recoil values, there is a significant difference between Example and Comparative Example. This suggests that the Comparative Example samples did not have sufficient radial force to support blood vessels.

For the above results, it was demonstrated that the design according to the present invention is suitable for a bioabsorbable stent having a scaffold made of a magnesium alloy to perform a predetermined function.

INDUSTRIAL APPLICABILITY

The present invention can provide a bioabsorbable stent having a sufficient strength, excellent durability, high flexibility as well as excellent expandability made of a bioabsorbable metal having low strength, i.e., even without materials having high strength such as stainless steel. Since the bioabsorbable stent according to the present invention has high flexibility and excellent expandability, no crack in a metal core or a polymer cover layer covering a metal core occurs at coupled portions in opposing cells and/or at a top of a circular arc part of a substantially U-shaped cell at the time of stent expansion. Accordingly, it is possible to provide a bioabsorbable stent which is less likely to have local corrosion of the bioabsorbable metal.

Although the present invention has been fully described in connection with the preferred embodiments thereof with reference to the accompanying drawings, those skilled in the art will readily conceive numerous changes and modifications within the framework of obviousness upon the reading of the specification herein presented of the present invention.

Accordingly, such changes and modifications are to be construed as included therein.

REFERENCE NUMERALS

1 . . . Stent
2, 2' . . . Cell
3, 3' . . . Cell group
4 . . . Coupling part (with a marker inserted)
4' . . . Coupling part (without a marker)
5, 5' . . . Circular arc part
6, 6' . . . Linear part
7 . . . Substantially linear coupling part
8 . . . Curved connecting part C1 . . . Central axis of a stent
a . . . Width of a substantially linear coupling part
b . . . Width of a curved connecting part
$w_T$ . . . Width of a cell line (arch) at a top of a circular arc part
$w_S$ . . . Width of a cell line (segment) at a substantially linear part
h . . . Cell height
w . . . Cell width
$q_S$ . . . Inclination angle
$r_O$ . . . Radius of curvature of an outer edge of a circular arc part

What is claimed is:

1. A bioabsorbable stent comprising:
a first tubular unit containing a first plurality of cells coupled to each other, each of the cells formed from substantially linear cell parts and a substantially semicircular arc part and having a substantially U-shape which opens in a first axial direction of the stent; and
a second tubular unit having the same shape as that of the first tubular unit, the second tubular unit containing a second plurality of cells opposing the first plurality of cells of the first tubular unit to form a plurality of opposing cell pairs, each of the plurality of cells of the second tubular unit having a substantially U-shape which opens in a second axial direction opposite to the first axial direction of the cells of the first tubular unit,
wherein:
a plurality of the first tubular units and the second tubular units are alternately arranged in sequence in a repeating pattern to define a stent having a central axis;
coupling members couple substantially linear cell parts in some of the plurality of opposing cell pairs;
the coupling members each comprising a substantially linear part and a curved connecting part, the curved connecting part having a width larger than a width of the substantially linear coupling part so that the substantially linear part of the coupling members are preferentially deformed instead of the curved connecting part upon stent expansion;
the first plurality of cells of the first tubular unit and the second plurality of cells of the second tubular unit are configured so that a ratio of a width ($w_T$) of a stent strut at the top of the semicircular arc part of the cells to a width ($w_S$) of a stent strut at the substantially linear cell part of the cells is within a range defined by the following formula (1):

$$1.1 < \text{width } (w_T) \text{ of a stent strut at the top of the semicircular arc part/width } (w_S) \text{ of a stent strut at the substantially linear cell parts} < 1.5 \quad (1);$$

a ratio of height (h) to width (w) of the first plurality of cells of the first tubular unit and the second plurality of cells of the second tubular unit is selected within a range defined by the following formula (2):

$$0.12 < \text{cell height } (h)/\text{cell width } (w) < 1.3 \quad (2);$$

And a maximum principal stress (σ max) upon stent expansion is selected to fall within a range defined by the following formula (3):

$$\text{Maximum principal stress (σ max) upon stent expansion} < \text{tensile strength } (S) \text{ of a material forming the bioabsorbable stent} \quad (3); \text{ and}$$

the bioabsorbable stent is formed of a stent material that comprises a bioabsorbable metal.

2. The bioabsorbable stent according to claim 1, wherein each cell of the first plurality of cells of the first tubular unit and the second plurality of cells of the second tubular unit have a thickness (t) selected so as to satisfy a range defined by the following formula (4):

$$0.06 \text{ mm} < t < 0.12 \text{ mm} \quad (4).$$

3. The bioabsorbable stent according to claim 1, wherein the semicircular arc part of each cell of the first plurality of cells of the first tubular unit and the second plurality of cells of the second tubular unit have a radius of curvature ($r_O$) selected so as to satisfy a range defined by the following formula (5):

$$0.15 \text{ mm} < r_O < 0.30 \text{ mm} \quad (5).$$

4. The bioabsorbable stent according to claim 1, wherein the substantially linear part of each cell of the first plurality of cells of the first tubular unit and the second plurality of cells of the second tubular unit have an inclination angle ($q_S$) with respect to a longitudinal axis of the stent selected so as to satisfy a range defined by the following formula (6):

$$30° < q_S < 90° \quad (6).$$

5. The bioabsorbable stent according to claim 1, wherein the bioabsorbable metal is pure magnesium or a magnesium alloy.

6. The bioabsorbable stent according to claim 1, wherein each of the curved connecting parts in the coupling members are connected to an intermediate portion of the substantially linear cell part of the some of the plurality of opposing cell pairs.

7. The bioabsorbable stent according to claim 1, wherein the curved connecting parts of the coupling members have a minimum radius of curvature in a range from 40 to 100 μm.

8. The bioabsorbable stent according to claim 2, wherein the semicircular arc part of the first plurality of cells of the first tubular unit and the second plurality of cells of the second tubular unit have a radius of curvature ($r_O$) selected so as to satisfy a range defined by the following formula (5):

$$0.15 \text{ mm} < r_O < 0.30 \text{ mm} \quad (5).$$

9. The bioabsorbable stent according to claim 2, wherein the substantially linear cell part of the first plurality of cells of the first tubular unit and the second plurality of cells of the second tubular unit have an inclination angle ($q_S$) with respect to a longitudinal axis of the stent selected so as to satisfy a range defined by the following formula (6):

$$30° < q_S < 90° \quad (6).$$

10. The bioabsorbable stent according to claim 3, wherein the substantially linear cell part of the first plurality of cells of the first tubular unit and the second plurality of cells of the second tubular unit have an inclination angle ($q_S$) with respect to a longitudinal axis of the stent selected so as to satisfy a range defined by the following formula (6):

$$30° < q_S < 90° \quad (6).$$

11. The bioabsorbable stent according to claim 8, wherein the substantially linear cell part of the first plurality of cells of the first tubular unit and the second plurality of cells of the second tubular unit have an inclination angle ($q_S$) with respect to a longitudinal axis of the stent selected so as to satisfy a range defined by the following formula (6):

$$30° < q_S < 90° \quad (6).$$

* * * * *